(12) United States Patent
Campbell

(10) Patent No.: US 7,022,486 B2
(45) Date of Patent: Apr. 4, 2006

(54) PEPTIDE SEQUENCE TAGS AND METHOD OF USING SAME

(75) Inventor: Douglas A. Campbell, c/o Department of Biology, Mount Allison Coastal Wetlands Institute, Mount Allison University, 63B York St., Sackville, New Brunswick (CA), E4L 1G7

(73) Assignee: Douglas A. Campbell, Sackville (CA)

( * ) Notice: Subject to any disclaimer, the term of this patent is extended or adjusted under 35 U.S.C. 154(b) by 397 days.

(21) Appl. No.: 10/216,810

(22) Filed: Aug. 13, 2002

(65) Prior Publication Data

US 2003/0096308 A1 May 22, 2003

Related U.S. Application Data

(60) Provisional application No. 60/312,042, filed on Aug. 13, 2001.

(51) Int. Cl.
*G01N 33/53* (2006.01)

(52) U.S. Cl. ........... 435/7.1; 435/7.95; 435/40.5; 435/69.7; 436/514

(58) Field of Classification Search ........... 435/7.1, 435/7.95, 40.5, 69.7; 436/514
See application file for complete search history.

(56) References Cited

U.S. PATENT DOCUMENTS 5,770,423 A * 6/1998 Beach et al. ............... 435/197
6,649,419 B1 * 11/2003 Anderson .................. 436/526

FOREIGN PATENT DOCUMENTS

US         WO 98/05687      *   2/1998

* cited by examiner

*Primary Examiner*—Long V. Le
*Assistant Examiner*—Jacob Cheu
(74) *Attorney, Agent, or Firm*—Eugene F. Derényi; Stikeman Elliott LLP

(57) ABSTRACT

Peptide sequence tags are identified and used to produce a class of global antibodies, which recognize all members of a particular protein family with uniform specificity, regardless of the species of origin. The tags are used to create antibodies to the major proteins of photosynthesis, and carbon and nitrogen metabolism. The antibodies have a range of applications as diagnostic detection reagents for major environmental processes.

2 Claims, 1 Drawing Sheet

*Ulmus* (elm)
*Synechococcus*
*Spartina* (marsh grass)
mixed phytoplankton
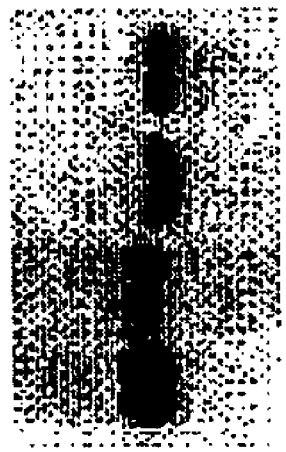

SEQUENCE LISTING

<160> NUMBER OF SEQ ID NOS: 16

<210> SEQ ID NO 1
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1

Glu Val Met His Glu Arg Asn Ala His Asn Phe Pro Leu Asp Cys
 1               5                  10                  15

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Leu Arg Gly Gly Leu Asp Phe Thr Lys Asp Asp Glu Asn Ile Asn
 1               5                  10                  15

Ser

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Thr Asn Ser Tyr Lys Arg Leu Val Pro Gly
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Glu Ser Gly Gly Pro Glu Pro Gly Val Gly Cys
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys His Phe Ser Trp Lys Met Gln Ser Asp Val Trp
 1               5                  10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

His Trp Thr Gly Cys Pro Asn Ser Cys
```

```
            1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Pro Lys Leu Gly Leu Ser Cys
 1               5

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Pro Lys Leu Gly Leu Ser Gly Lys Asn Tyr Gly Arg Cys
 1               5                  10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Leu Phe Glu Glu Gly Ser Cys
 1               5

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Phe Ala Glu Val Gly Arg Arg Leu Gly Phe
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Ser Gln Ser Leu Gly His His Ile Ala Asn Asp
 1               5                  10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
                               -continued peptide

<400> SEQUENCE: 12

Cys Thr Thr Cys Met Ala Glu Val Ile Gly Asp Asp Leu
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Met Ala Glu Val Ile Gly Asp Asp Leu
 1               5                  10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Arg Gln Trp Glu Leu Cys
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Arg Glu Trp Glu Leu Cys
 1               5

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Phe Pro Cys Asp Gly Pro Gly Arg Gly Gly Thr Cys
 1               5                  10
```

PEPTIDE SEQUENCE TAGS AND METHOD OF USING SAME

This application claims the benefit of Provisional Application No. 60/312,042, filed Aug. 13, 2001.

This invention relates to peptide sequence tags used to elicit antibodies, which can be used to detect defined families of proteins.

Natural populations of phytoplankton include representatives of numerous species of cyanobacteria, diatoms, green algae and other groups. Nevertheless many of these species share core biochemical pathways supporting primary productivity and elemental cycling (Bryant, 1994; Falkowski & Raven, 1997). To assess the gross capacity for key metabolic transformations in aquatic habitats, and to track acclimatory changes in these capacities, researchers require reagents to quantitatively detect all members of a functional class of enzymes (Bouchard et al., 2002; Schofield et al., 2002), for example the RbcL (RUBISCO) enzyme responsible for carbon fixation in all photosynthetic organisms. Different members of the organism population will contain somewhat different versions of the RbcL enzyme, which nevertheless share similar core properties and shared conserved regions (ncbi.nlm.nih.gov). Conventional immunological detection uses an antibody raised against one particular protein from one species, which will then bind with variable affinity to other related proteins depending on their antigenic similarity to the initial target molecule (Orellana & Perry, 1992). This is problematic because change in immunological signals could result from: a) changes in the level of the targets b) changes in the population composition resulting in shifts in the specific mix of target molecules present or c) a combination of (a) and (b).

Conventional antibodies are raised against two classes of protein targets; namely (a) purified or over-expressed protein from a particular species, and (b) a peptide selected to match the sequence of a region of a particular protein. Such antibodies are generally raised against proteins from a model species, and show variable cross-reactivity to related proteins from other species. It is not practical to develop individual antibodies to detect each protein of interest from each strain in a population, many of which are poorly characterized or unknown, and even unculturable (Staley & Reysenbach 2002). Most of the protein families of interest in cyanobacteria and phytoplankton are also highly conserved in plants so that the same detection system can meet needs for standard antibodies in plant sciences.

Thus, a need exists for a set of peptide targets to elicit production of a set of antibodies to detect key proteins involved, inter alia, in photosynthetic activity. A system should be able to evenly and universally recognize all members of a defined enzyme family or subfamily based on shared characteristics.

The above defined need is met by the present invention which provides a method for detecting the presence of members of the target protein family in a sample comprising the steps of:
 (a) identifying and obtaining a peptide sequence tag conserved for all sequences of members of the target protein family, and exclusive to the target protein family;
 (b) assessing the tag for immunogenicity potential
 (c) utilizing the tag to elicit the production of antibodies; and
 (d) using the antibodies to measure the concentration of members of the target protein family in a sample.

The invention also provides a peptide sequence tag selected from the group consisting of

| | |
|---|---|
| SEQ ID NO: 1 | SEQ ID NO: 9 |
| SEQ ID NO: 2 | SEQ ID NO: 10 |
| SEQ ID NO: 3 | SEQ ID NO: 11 |
| SEQ ID NO: 4 | SEQ ID NO: 12 |
| SEQ ID NO: 5 | SEQ ID NO: 13 |
| SEQ ID NO: 6 | SEQ ID NO: 14 |
| SEQ ID NO: 7 | SEQ ID NO: 15 |
| SEQ ID NO: 8 | SEQ ID NO: 16 |

In accordance with another aspect of the invention, the invention provides a method for detecting the presence of a target protein in a sample comprising the steps of:
 (a) identifying and obtaining a peptide sequence tag conserved for all members of and exclusive to a protein family;
 (b) assessing the tag for immunogenicity; and
 (c) synthesizing the tag provided it possesses a predetermined level of immunogenicity.
 (d) utilizing the tag to elicit the production antibodies; and
 (e) using the antibodies to provide an indication of protein concentration in a sample.

According to yet another aspect, the invention provides a method of using a peptide sequence tag for coupling to column matrice materials for affinity purification of the global antibodies produced according to the invention.

According to yet another aspect, there is provided a method of developing characterized concentration standards for quantitation of the concentration of target proteins in samples by comparison to the concentration standards comprising the steps of;
 (a) coupling a defined molar quantity of protein carrier molecule to a defined molar quantity of peptide sequence tag selected from the group consisting of

| | |
|---|---|
| SEQ ID NO: 1 | SEQ ID NO: 9 |
| SEQ ID NO: 2 | SEQ ID NO: 10 |
| SEQ ID NO: 3 | SEQ ID NO: 11 |
| SEQ ID NO: 4 | SEQ ID NO: 12 |
| SEQ ID NO: 5 | SEQ ID NO: 13 |
| SEQ ID NO: 6 | SEQ ID NO: 14 |
| SEQ ID NO: 7 | SEQ ID NO: 15 |
| SEQ ID NO: 8 | SEQ ID NO: 16 |

(b) subjecting a known molar quantity of the coupled complex from (a) to electrophoretic separation in parallel SDS-PAGE gel lanes with protein extracts containing members of the target protein family, followed by electrophoretic transfer to a membrane
(c) immunodetection using a global antibody produced according to the above-defined method of the coupled standard and any members of the target protein family identified by the peptide sequence tag and
(d) using an immunological signal from the known molar quantity of coupled complex as a standard for measuring the molar quantity of members of the target protein family present in the protein extracts.

In a still further aspect, there is provided a method for quantitation of members of the target protein families in multiple samples using Enzyme-Linked ImmunoSorbent Assay kits using on characterized global antibodies produced according to the above-defined method and quantitation standards produced according to the method defined in the preceding paragraph.

In another aspect, there is provided a method for eliciting production of monoclonal, transgenic or synthetic antibodies using peptide sequence tags produced according to the above defined method and standard immunological protocols.

In a further aspect, there is provided a method for affinity screening of libraries of reagents to detect specific reagent binding to a peptide sequence tag produced according to the above defined method and immobilized on a support matrice; and testing reagents binding to the immobilized peptide sequence tag for affinity binding to members of the target protein families.

In a still further embodiment, there is provided a method to use affinity binding using global antibodies produced according to the above-defined method to capture target proteins from complex mixtures for subsequent analyses of the specific sequences of target proteins present in the mixture using mass spectroscopy.

In yet another embodiment, there is provided a method to use affinity binding using global antibodies produced according to the above defined method to capture and remove target proteins from complex mixtures to lower interference with detection and analyses of other less abundant protein classes in proteomics applications such as two dimensional isoelectric focusing/SDS-PAGE and subsequent mass spectroscopic analyses of protein sequences.

In general terms, the inventors have designed a set of peptide targets or peptide sequence tags which elicit production of a set of antibodies for detecting key proteins involved in photosynthetic productivity. The inventors chose target protein families based on scientific interest and wide applicability. They have found and aligned sequences from public databases to detect peptide sequence tags of 6–25 amino acids which are conserved in all known members of the target protein family, and use bioinformatic analyses to determine if the conserved peptides are unique to the target protein family. The peptide sequence tags are assessed for potential immunogenicity, feasibility of synthesis, solubility and stability; avoiding sequences that are targets for known or putative post-translational modification in proteins. Selected peptide sequence tags are synthesized, coupled to a carrier and used to elicit antibody production. The specificity and titre of the antibodies were then listed. A set of antibodies increases the utility of the system by allowing comprehensive detection of key molecules in a sample, population or community. The target protein families were selected based on their core roles in the biosphere and their interest and importance for environmental research, modelling, and monitoring.

Public sequence databases were scanned for all published sequences of proteins in a given family (http://www.expasy.ch; http://www.ncbi.nlm.nih.gov). The sequences of all published members of each target protein family were aligned (Corpet, 1988). Peptide sequence tags of 6–25 amino acids were selected whose sequences are conserved in all known members of the target protein or sub-family. The peptide sequence tags were tested to determine exclusivity to the target protein family using short-peptide BLAST searches of sequence databases (Altschul et al., 2001). The position of each potential peptide sequence tag in a given protein family was analyzed to ensure it is maintained in the mature proteins, and to avoid regions of the proteins known or suspected to undergo post-translational modifications such as glycosylation that could interfere with later antibody recognition of the mature proteins. The peptide sequence tags are screened for antigenic potential using peptide property prediction algorithms, and to assess their feasibility for syntheses, solubility and stability based on amino acid composition. In summary the chosen peptide sequence tags are conserved in all published members of the defined target protein family or subfamily, do not align significantly with members of other known protein families, and have acceptable predicted antigenic and synthesis properties The selected peptide sequence tags are synthesized. The peptide sequence tags are then coupled to appropriate immunogenic carrier molecules, typically Keyhole Limpet Hemocyanin, and the complexes are used to elicit production of IgY antibodies in hens. The IgY fraction is separated from the eggs of the immunized hens and the fraction is screened using Enzyme-Linked ImmunoSorbent Assays (ELISA) for binding to the original peptide target. Each IgY production run generates sufficient antibody for hundreds of thousands of immunodetections. Additional hens can be immunized to generate further comparable antibody preparations and for pooling of antibody preparations from multiple hens.

Members of the target protein family are extracted from a range of species, separated by SDS-polyacrylamide gel electrophoresis, electrophoretically transferred to membranes and immnunoblotting is used to characterize the binding of the antibodies to a range of members of the target protein family. Antibody preparations with good target affinity but which show non-specific binding to other proteins are subjected to affinity purification followed by re-characterization to attempt to improve specificity.

The novel antibodies can be applied to detect major proteins in a range of species, including uncharacterized species, with confidence that the detection affinity of the antibody is standard for all denatured members of the target protein family. Therefore a quantity standard protein from one species or a synthetic quantity standard can be used for comparative quantitation of members of the protein family from other species.

DETAILED DESCRIPTION OF INVENTION

Peptide sequence tags designed for eliciting production of global antibodies binding all members of defined protein families or subfamilies.

In the following, all peptides are written according to convention from amino terminus to carboxy terminus using the standard single letter amino acid code. All peptides are based on alignments of protein sequences accessed through the NCBI (ncbi.nlm.nih.gov) and SwissProt (expasy.ch) public databases. Where present a lower-case "c" indicates a terminal cysteine not present in the original protein family but added for chemical coupling to the immunogenic carrier molecule, usually Keyhole Limpet Hemocyanin. An upper case terminal "C" represents a cysteine present in the original protein, but also used for chemical coupling to the immunogenic carrier molecule.

1. PsbA: EVMHERNAHN FPLDc (SEQ ID NO:1) Photosystem II is the ultimate source of almost all biosynthetic reductant in the biosphere. The PsbA (D1) protein of Photosystem II is rapidly cycled under illumination in all oxygenic photobionts (Aro et al., 1993). Disruptions of PsbA cycling or losses of PsbA pools are central to loss of Photosystem II function and consequent photoinhibition of photosynthesis in cyanobacteria, algae and plants under a wide range of conditions including excess light, low temperature and UV exposure (e.g. Bouchard et al., 2002; Campbell et al., 1998). Tracking PsbA pools using the global PsbA antibody elicited by the PsbA peptide sequence tag can show the functional content of Photosystem II in a wide range of samples.

This PsbA peptide sequence tag is absolutely conserved in the PsbA proteins from almost all known oxygenic photoautotrophs, with only minor variants found in some liverworts. The global antibody raised against this PsbA peptide sequence tag has to date been demonstrated to specifically recognize the PsbA protein from a wide range of species including plants, red algae, cyanobacteria, green algal lichens and a mixed natural phytoplankton community. For example the antibody is being applied to a biological oceanography project to study UV acclimation in natural phytoplankton at sites from the Arctic to the Antarctic (Bouchard et al., 2002), and also to a study of seasonal acclimation in lichens (Schofield et al., 2002).

2. RbcL: CLRGGLDFTK DDENINS (SEQ ID NO:2) RbcL (RUBISCO) is the catalytic subunit of the primary carbon dioxide fixation enzyme in the biosphere and is present in all photobionts, along with many other prokaryotic organisms that fix carbon through chemoautotropic mechanisms. The kinetic properties of RbcL are well characterized and the activity of RbcL limits total carbon dioxide uptake by many communities (e.g. Badger & Andrews, 1987; von Cammerer & Quick, 2001). The enzyme has a low turnover rate (low kcat) but because the total flux of carbon fixation through the enzyme is large in photosynthetic organisms, the enzyme accumulates to high concentrations (e.g. 5–10% of extractable protein in cyanobacteria). It is thus a major sink for nitrogen and protein resources in photosynthetic organisms, and is indeed the most abundant protein on earth and a major protein source in the human diet, either directly through consumption of green plants or through contributions to forage feed for animals. Quantitating RbcL thus shows the total capacity for carbon uptake in a sample or community. This RbcL peptide sequence tag is diagnostic of tie Type I sub-class of RUBISCO found in almost all oxygenic photoautotrophic organisms with the exception of dinoflagellates and the marine prochlorophyte *Prochlorococcus*. This RbcL peptide sequence tag is absolutely conserved in all known sequences from cyanobacteria, green algae, liverworts, mosses, conifers, eudicots, and monocots. The RbcL peptide sequence tag is conserved perfectly in some species, but shows minor variants in some species of ferns, euglenoids, gamma-proteobacteria, beta-proteobacteria, alpha-proteobacteria. It is present but imperfectly conserved in red algae, diatoms, cryptomonads, haptophytes and brown algae. The global antibody raised against this RbcL peptide sequence tag has to date been demonstrated to specifically recognize the RbcL protein from a wide range of species including cyanobacteria, green algal lichens, various plants and a mixed phytoplankton community dominated by diatoms.

IN THE DRAWING

The accompanying drawing shows the results of an immunoblot chemiluminescent detection of RbcL protein in total protein extracts from (a) an elm tree, (b) cyanobacterium (*Synechococcus* sp. PCC 7942), (c) marsh grass (*Spartina*) and (d) mixed population of marine phytoplankton from the Gulf of St. Lawrence, dominated by diatoms.

Total denatured protein extracts from the four samples were separated by SDS-PAGE and electrophoretically transferred to hydrophobic membrane, The membrane was washed with a 1:4000 dilution of the global RbcL IgY antibody fraction (non-affinity purified) using standard immunoblotting procedures and solutions (Ausubel et al., 1997). The Global RbcL antibody was then detected using a commercial secondary goat anti-chicken IgY antibody conjugated to a horse radish peroxidase enzyme label. Finally, the areas with bound horse radish peroxidase were detected using ECL+ (Amersham Pharmacia) chemiluminescent.

The drawing illustrates the broad detection range and examples of the three main utilities of the new global antibodies raised against peptide sequence tags; namely (a) detection of a major protein from organisms (elm and *Spartina*) which are relatively uncharacterized at the molecular level but which are of ecological interest, (b) detection of the same protein from a widely studied model species, the cyanobacterium *Synechococcus,* and (c) detection of the same protein family from a mixed phytoplankton community.

Application (c) is part of a study of natural phytoplankton responses to changing UVB (Bouchard et al., 2002), where both the absolute level of the target protein and the community structure change under UVB exposure, necessitating an antibody with even detection efficiencies for all members of the target protein family.

3. GlnA: cTNSYKLVP G (SEQ ID NO:3) GlnA or glutamine synthetase is the primary point for assimilation of inorganic ammonia nitrogen into the biosphere. During nitrogen assimilation all nitrogen sources are converted to ammonia, no matter what the original source, and then assimilated predominately via the activity of glutamine synthetase. Thus tracking levels of glutamine synthetase shows the metabolic capacity of a sample or community for total nitrogen assimilation.

This GlnA peptide sequence tag shows perfect to high conservation in alpha, beta and gamma proteobacteria, enterobacteria, most cyanobacteria, thermotogales, low GC gram+, euryarchaeotes and crenarchaeotes. It shows moderate conservation with aquificales, high GC gram+ (*Streptomyces*) and *Trichodesmium thiebautii* (a marine cyanobacteria).

The GlnA peptide sequence tag shows weak and sporadic conservation with glutamine synthetase Type III (GlnN) and with some glutaminyl-tRNA synthetases (glutamine-tRNA ligase) (GLNRS), but antibodies raised against this peptide sequence tag are not expected to detect these enzymes. This peptide sequence tag shows no conservation with any eukaryotic GlnA, and therefore does not react with glutamine synthetases from eukaryotic sources. The global antibody raised against this GlnA peptide sequence tag has to date been demonstrated to specifically recognize the GlnA protein from several species of cyanobacteria.

4. NifH: VESGGPEPGV GC (SEQ ID NO: 4) The NifH subunit is a component of the unstable nitrogenase enzyme system responsible for biological fixation of $N_2$ to assimilable ammonia. Levels of the NifH protein can be used to track the total potential metabolic capacity for nitrogen fixation in any sample or community. This NifH peptide sequence tag is perfectly or near-perfectly conserved in NifH proteins from all known organisms including: alpha, gamma, beta proteobacteria, enterobacteria, cyanobacteria, low GC gram+ bacteria, high GC gram+ bacteria, euryarchaeotes.

5. PsaA: cHFSWKMQSD VW (SEQ ID NO 5) PsaA is a core subunit of Photosystem I, a key complex involved in transduction of light to chemical energy in all oxygenic photobionts. Photosystem I participates in both linear and cyclic electron transport in photoautotrophic organisms. The molar ratio between Photosystem II and Photosystem I varies widely between taxa and under different environmental conditions (Falkawski & Raven, 1997), and is an important factor for inferring the acclimation state and photosynthetic performance of an organism or a community. This PsaA peptide sequence tag is specific to the sequence of the PsaA core protein of Photosystem I from all known photoautotrophic organisms, with the exception of a single amino acid mismatch at the third position in the dinoflagellate *Heterocapsa triquetra*.

6. NirB: HWTGCPNSC (SEQ ID NO: 6) NirB or nitrite reductase catalyzes the reduction of nitrite to ammonia, which is an obligatory intermediary step in assimilation of inorganic nitrate into the biosphere. Nitrate is the dominant source of inorganic nitrogen supporting primary productivity in most ecosystems and hence tracking NirB levels show the metabolic capacity for assimilation of this key nitrogen source involved in eutrophication, agricultural run-off and stimulation of algal blooms including harmful (toxic) algal blooms.

7. RbcL185: KPKLGLSc (SEQ ID NO: 7) This peptide sequence tag is conserved in both Type I and Type II RbcL and hence can be applied to raise antibodies that will recognize both classes of RUBISCO enzyme, including the RUBISCO found in dinoflagellates and the zooxanthellae symbionts of coral.

8. RbcL185a. KPKLGLSGKN YGRc (SEQ ID NO: 8) This peptide sequence tag is conserved in Type I RUBISCO and could be applied to generate a second anti-RUBISCO antibody for use in ELISA sandwich assays.

9. RbcL115: DLFEEGSc (SEQ ID NO: 9) This peptide sequence tag is conserved in Type I RUBISCO and could be applied to generate a second anti-RUBISCO antibody for use in ELISA sandwich assays.

10. NarB: IFAEVGRRLG F (SEQ ID NO: 10) This peptide sequence tag is specific to the nitrate reductase (NarB) enzyme from cyanobacteria, a key enzyme in nitrate assimilation.

11. NifDMo: VSQSLGHHIA ND (SEQ ID NO: 11) This peptide sequence tag is specific to the NifD subunit of the sub-set of nitrogenases with an iron/molybdenum-based co-factor (as opposed to iron/vanadium or pure iron cofactors).

12. NifKMo: CTTCMAEVIG DDL (SEQ ID NO: 12) This peptide sequence tag is specific to the NifK subunit of the sub-set of nitrogenases with an iron/molybdenum-based co-factor (as opposed to iron/vanadium or pure iron cofactors).

13. NifKMo: CMAEVIGDDL (SEQ ID NO: 13) This peptide sequence tag is an alternate target specific to the NifK subunit of the sub-set of nitrogenases with an iron/molybdenum-based co-factor (as opposed to iron/vanadium or pure iron cofactors).

14. PsbA1: GRQWELc (SEQ ID NO: 14) This peptide sequence tag is specific to cyanobacterial PsbA1, a form of PsbA expressed in acclimated cyanobacteria, but not in eukaryotic photobionts (plants and algae). Monitoring this protein can thus track the contribution of acclimated cyanobacteria to Photosystem II light energy conversion in a mixed community.

15. PsbA2 GREWELc (SEQ ID NO: 15) This peptide sequence tag is specific to cyanobacterial PsbA2, a form of PsbA expressed only in cyanobacteria experiencing excitation stress or UVB stress (e.g. Campbell et al., 1998). Monitoring this protein can thus tack when a cyanobacterial population is under excitation or UVB stress. It is also specific to the sole constitutive form of PsbA in eukaryotic photobionts (plants and algae).

16. PsaB: FPCDGPGRGG TC (SEQ ID NO: 16) This peptide sequence tag is specific to the PsaB core protein of Photosystem I, a key complex involved in transduction of light to chemical energy in all oxygenic photobionts.

References

Altschul S et al. (2001) http://www.ncbi.nlm.nih.gov/BLAST

Aro E M et al. (1993) Biochim Biophys. Acta 1143:113–134

Ausubel F et al. (1997) Short Protocols in Molecular Biology, Wiley, New York.

Badger M R, Andrews T J (1987) Progress in Photosynthesis Research Vol. III. Martinus Nijhoff Publishers, pp 601–609.

Bouchard J N et al. (2002) American Society of Photobiology, Quebec, Canada

Bryant D (ed,) (1994) *The Molecular Biology of Cyanobacteria*, Kluwer Academic.

Campbell D et al. (1998) Proceedings of the National Academy of Sciences of the USA 95:364–369.

Corpet F (1988) Nucleic Acids Research 16 (22): 10881–10890. http/www.expasy.ch SwissProt public database of annotated protein sequences and accompanying proteomic analysis tools.

Falkowski P G & Raven J A (1997) *Aquatic Photosynthesis*. Blackwell Science. http://www.ncbi.nlm.nih.gov Searches for the target protein families show a range of representatives from different taxonomic groups, nonetheless sharing key conserved regions and core biochemical functions.

Orellana M V & Perry M J (1992) *Limnology & Oceanography* 478–490

Schofield S C et al. (2002) in revision.

Staley J T & Reysenbach A-L (eds.) (2002) *Biodiversity of Microbial Life*. Wiley-Liss.

von Caemmerer, S. & Quick, W. P. (2000) In *Photosynthesis: Physiology and Metabolism*, (ed. R. C. Leegood, T. D. Sharkey, and S. von Caemmerer), Kluwer.

I claim:

1. A method for detecting the presence of a PsbA protein (photosynthesis II protein A) in a sample comprising the steps of:
   (a) identifying and obtaining a peptide sequence tag conserved for the PabA protein, and exclusive to the PsbA protein wherein said peptide sequence tag is SEQ ID NO: 1, SEQ ID NO:14 or SEQ ID NO:15 ;
   (b) utilizing the tag to elicit the production of antibodies; and
   (c) using the antibodies to measure the concentration of PsbA protein in a sample.

2. A isolated peptide sequence tag consists the sequence of

SEQ ID NO: 1
SEQ ID No: 14
and
SEQ ID No: 15.

* * * * *